United States Patent [19]
Nevyas

[11] Patent Number: 5,618,261
[45] Date of Patent: Apr. 8, 1997

[54] EYE PROPTOSING SPECULUM AND METHOD

[76] Inventor: Herbert J. Nevyas, 1120 Tower La. East, Narberth, Pa. 19072

[21] Appl. No.: 330,513

[22] Filed: Oct. 27, 1994

[51] Int. Cl.$^6$ ............................................. A61B 19/00
[52] U.S. Cl. ............................................. 600/236; 606/107
[58] Field of Search ................................. 128/20; 600/236

[56] References Cited

U.S. PATENT DOCUMENTS

| | | | |
|---|---|---|---|
| 1,230,873 | 6/1917 | Crossley | 600/236 |
| 1,237,121 | 8/1917 | Suffa | 600/236 |
| 1,706,500 | 3/1929 | Smith . | |
| 2,075,534 | 3/1937 | McCormack | 600/219 |
| 2,438,646 | 3/1948 | Pulliam | 600/236 |
| 2,702,540 | 2/1955 | Debeh | 128/20 |
| 4,037,589 | 7/1977 | McReynolds | 128/20 |
| 4,321,916 | 3/1982 | McKee | 128/20 |
| 4,412,532 | 11/1983 | Anthony | 128/20 |
| 4,579,116 | 4/1986 | Catalano | 600/236 |
| 5,054,906 | 10/1991 | Lyons, Jr. | 351/205 |
| 5,070,860 | 12/1991 | Grounauer | 128/20 |
| 5,171,254 | 12/1992 | Sher | 606/166 |
| 5,213,114 | 5/1993 | Bailey, Jr. | 128/849 |
| 5,290,292 | 3/1994 | Householder | 606/107 |
| 5,341,798 | 8/1994 | Grounauer | 600/236 |
| 5,441,040 | 8/1995 | Williams, Jr. | 600/236 |

FOREIGN PATENT DOCUMENTS 1124917  11/1984  U.S.S.R. ................................ 600/236

*Primary Examiner*—Lynne A. Reichard
*Assistant Examiner*—Kelly McGlashen
*Attorney, Agent, or Firm*—Panitch Schwarze Jacobs & Nadel, P.C.

[57] ABSTRACT

An eye proptosing speculum that applies pressure to urge the eyeball outwardly is disclosed. The speculum includes a pair of blades and a pair of pressors. The pair of blades are opposingly situated and extend generally posteriorly. Each blade is shaped to engage the patient between one of the eyelids and the eyeball. The pair of pressors are also opposingly situated and extend generally posteriorly. One pressor extends from each blade and each pressor is shaped to engage and to exert pressure on the peripheral orbital contents. The pressure is transferred to the posterior orbital contents and then to a posterior region of the eyeball to proptose the eyeball outwardly. Each blade and each pressor, in combination, generally extend to follow the exterior surface of the eyeball, and each blade and each pressor is shaped to minimize extrinsic pressure directly on the eyeball. The eye proptosing speculum has a pair of arms attached to and cooperating with each other, with one blade being attached to each of the arms. Preferably, the speculum has an adjustment device for adjustably fixing the distance between the free ends of the arms.

10 Claims, 1 Drawing Sheet

EYE PROPTOSING SPECULUM AND METHOD

FIELD OF THE INVENTION

The present invention relates to a speculum for use in eye surgery. More particularly, the invention relates to a speculum that proproses an eyeball during eye surgery (moves the eyeball outwardly from the eye orbit) to allow greater access to the exposed surface of the eyeball.

BACKGROUND OF THE INVENTION

When performing eye surgery, it may be necessary to hold back the upper and lower eyelids by way of an eye speculum. Such an eye speculum may comprise a two-armed instrument with an adjusting device for finely adjusting the angle of one arm with respect to the other. Additionally, such an eye speculum has a retractor or blade at the distal end of each arm that may comprise a scoop-shaped piece in cross-section. Each scoop is inscribed around and under a respective eyelid, and the eye speculum holds the eyelids back when the adjusting device is adjusted to open the angle between the arms. Normally, an eye speculum is designed and employed such that pressure is not exerted on the eyeball since pressure tends to distort the eyeball. Moreover, excessive pressure may cause protrusion of the ocular contents and thereby complicate intraocular surgery.

When performing certain surgical procedures on the eye which do not involve opening the eyeball, it is preferable to proprose the eyeball outwardly to expose more of the surface of and allow greater access to the eyeball. An example of such a surgical procedure is an automated lamellar keratectomy (ALK), where a relatively large vacuum fixation ring is applied to the front surface of the eyeball. As may be understood, the application of the ring is more easily performed when greater exposure of the front surface of the eyeball is provided.

Accordingly, it would be advantageous to provide a surgical instrument that safely and easily proproses the eyeball outwardly to allow greater access to the exposed surface of the eyeball during eye surgery.

SUMMARY OF THE INVENTION

The present invention is directed to an eye proptosing speculum that applies pressure to the retrobulbar orbital contents surrounding the eyeball to push the eyeball outwardly. The eye proptosing speculum includes a pair of eyelid scoops or blades and a pair of pressors. The pair of blades are opposingly situated with respect to each other and extend generally posteriorly. Each blade has a posterior area and is shaped to engage the patient between one of the eyelids and the eyeball. The pair of pressors are also opposingly situated with respect to each other and extend generally posteriorly. One pressor extends from each blade at the posterior area thereof, and each pressor is shaped to engage and to exert pressure on a peripheral portion of the orbital contents. The pressure exerted by the pressors and also by the blades is transferred by the peripheral portion to a posterior portion of the orbital contents and then to a posterior region of the eyeball to proprose the eyeball outwardly.

Preferably, the portion of each blade adjacent the exterior surface of the eyeball and each pressor, in combination, generally extend to follow the exterior surface of the eyeball. Accordingly, each blade and each pressor is shaped to minimize extrinsic pressure directly on the eyeball.

Preferably, the eye proptosing speculum also includes a pair of arms connected to one another by an adjusting device, where each arm has a free end spaced an adjustable distance from the free end of the other arm. Accordingly, one blade is attached to each of the arms proximate the free end thereof. Preferably, the adjusting device adjustably fixes the distance between the free ends of the arms, and is an adjustable screw mechanism.

BRIEF DESCRIPTION OF THE DRAWINGS

The foregoing summary, as well as the following detailed description of a preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings:

FIG. 2a shows the eyeball without pressure being applied by the speculum and FIG. 2b shows the eyeball with pressure being applied by the speculum.

DETAILED DESCRIPTION OF PREFERRED EMBODIMENTS

Figure 1:
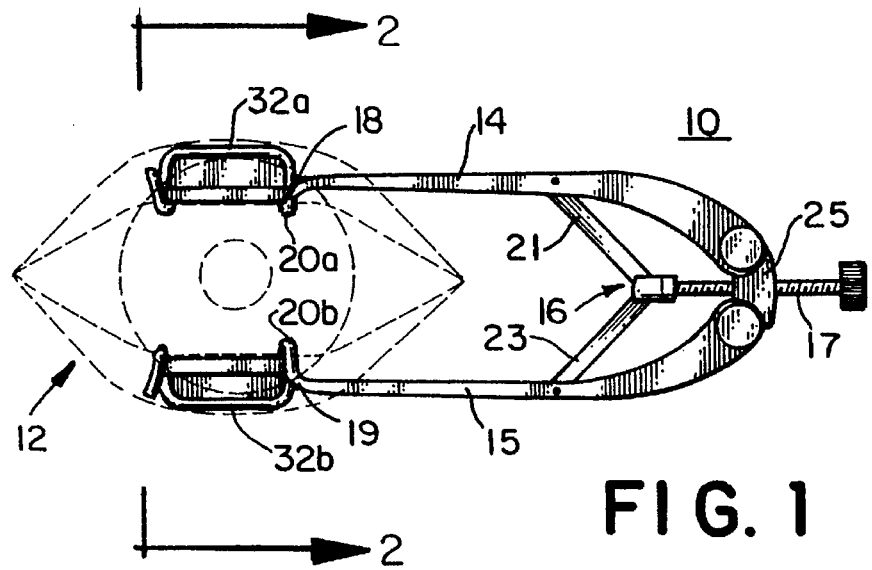
FIG. 1 is a perspective view of an eye proptosing speculum positioned with respect to an eyeball of a patient.

Certain terminology may be used in the following description for convenience only and is not limiting. The words "left", "right", "upper", and "lower" designate directions in the drawings to which reference is made. The words "inwardly" and "outwardly" are further directions toward and away from, respectively, the geometric center of the referenced object. The terminology includes the words above specifically mentioned, derivatives thereof, and words of similar import.

Referring to the drawings in detail, wherein like numerals are used to indicate like elements throughout, there is shown in FIG. 1 an eye proptosing speculum 10 positioned with respect to an eye 12 of a patient. Speculum 10 has a pair of arms 14, 15 that are connected to one another by way of an adjusting device 16. As seen in FIG. 1, the adjusting device 16 may be an adjustable screw mechanism having a screw 17 threaded through the center of a bridge 25. Each arm 14, 15 is pivotally attached to the bridge 25 at either end of the bridge 19, and a pair of struts 21, 23 are pivotally attached to and extend from the distal end of the screw 17. Each strut 21, 23 is also pivotally attached to a respective arm 14, 15 of the speculum 10. By rotating the screw and moving the struts, the free ends 18, 19 of the arms 14, 15 may be spaced an adjustable distance from each other. Further, since pressure on the arms 14, 15 will tend not to rotate the screw 17, the geometry of the adjusting device 16 fixes the adjustable distance until the screw 17 is rotated.

Preferably, the adjusting device 16 adjustably fixes the distance between the free ends 18 of the arms 14. However, the ability to adjustably fix the distance is not crucial to the present invention, and non-fixing devices may also be employed. As one skilled in the art will recognize, any of several well-known adjusting mechanisms may be employed instead of the adjusting device 16 while still being within the spirit and scope of the present invention.

Figure 2A:
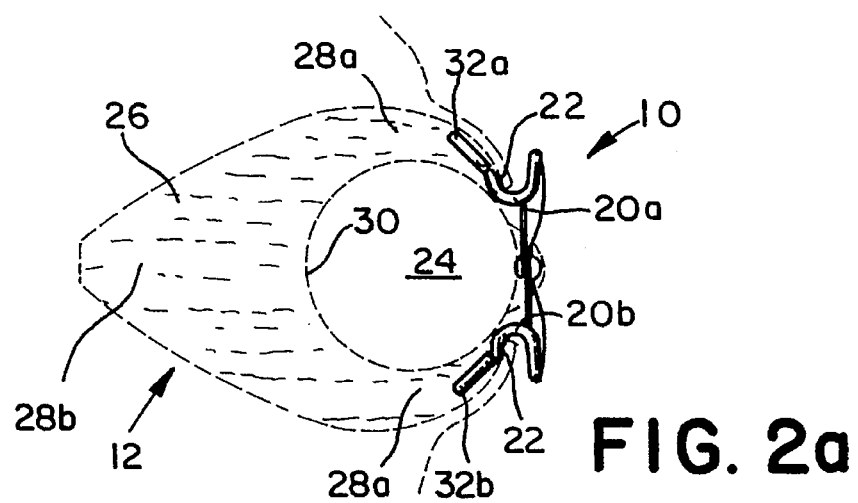
FIGS. 2a and 2b are cross-sectional views taken along the line 2—2 of FIG. 1, where
Figure 2B:
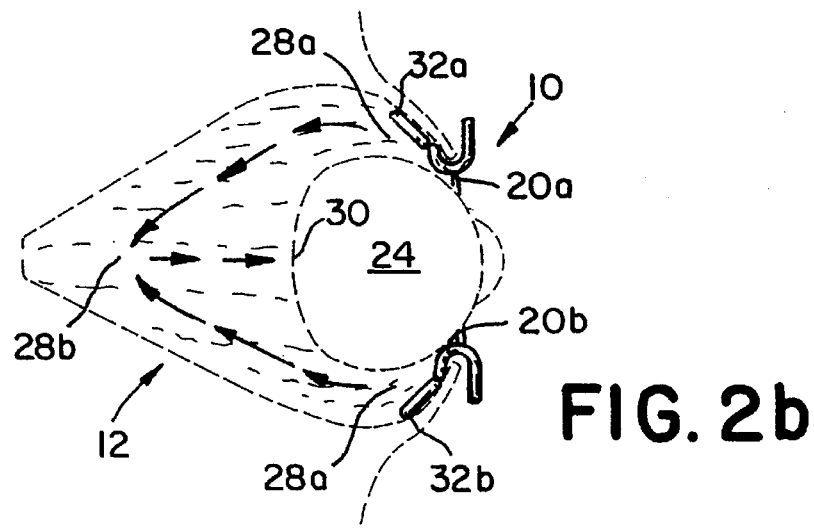

As may be seen in cross section in FIG. 2a, the speculum 10 has a pair of scoops or blades 20a, 20b, one blade 20a, 20b extending from the free end 18, 19 of each arm 14, 15, respectively. More particularly, each blade 20a, 20b is generally curved or U-shaped in cross section to engage the eye 12 between one of the eyelids 22 and the eyeball 24. As seen in FIGS. 2a and 2b, the blades 20a, 20b extend generally posteriorly or toward the eyeball 24 from the free ends 18, 19 of the arms 14, 15 when the speculum 10 engages the eye 12 of the patient.

As is well known and as is shown in FIGS. 2a and 2b, the eyeball 24 is positioned within an eye orbit 26 and, at least with regard to unexposed surfaces, is substantially surrounded by retrobulbar orbital contents 28a, 28b. The contents 28a, 28b includes such materials as eye muscles, fatty deposits, and other matter normally found in the area between the eyeball 24 and the eye orbit 26.

As may be understood, when inward pressure is applied to the accessible anterior portions of the peripheral orbital contents 28a, the pressure is transferred by the peripheral contents 28a to the posterior orbital contents 28b and then to a posterior region 30 of the eyeball 24 to proprose the eye outwardly. As seen in FIG. 2b, arrows are employed to represent the forces caused by such inward pressure.

Accordingly, and in order to exert the necessary pressure on the peripheral portions of the peripheral contents 28a, the speculum 10 has a pair pressors 32a, 32b. As seen in FIGS. 2a and 2b, each pressor 32a, 32b is opposingly situated with respect to the other and extends generally posteriorly or toward the eyeball 24 from each blade 20a, 20b, respectively. When positioned with respect to the eye 12, each pressor 32a, 32b engages a part of the peripheral contents 28a. As also seen in FIGS. 2a and 2b, each pressor 32a, 32b extends behind each respective eyelid 22 approximately 15 millimeters along the eyeball 24 in order to engage the accessible anterior portions of the peripheral orbital contents 28a. Thus, when the adjusting device 16 is adjusted to increase the distance between the free ends 18 of the arms 14 and when pressure is inwardly applied to the peripheral orbital contents 28a by way of the blades 20, the pressors 32 and the speculum 10, the eyeball 24 is proprosed outwardly about four to six millimeters.

Preferably, the patient is lying on his or her back and the inward pressure is applied manually by pressing downwardly on the speculum 10. More preferably, the adjusting device 16 is sturdily constructed such that downward finger pressure may be applied on the adjusting device 16 in the area of the juncture of the screw 17 and the struts 21, 23. Also preferably, each blade 20a, 20b and each pressor 32a, 32b is shaped to minimize extrinsic pressure directly on the eyeball 24 and to maximize pressure directly on the peripheral contents 28a. Specifically, it is preferable that the portion of each blade 20 adjacent the exterior surface 34 of the eyeball 24 and each pressor, in combination, generally extend to follow the curvature of the exterior surface 34 of the eyeball 24. Accordingly, if each pressor 32a, 32b is formed from a sheet of material, the material has a concave shape.

Preferably, the speculum 10 is constructed from one or more durable, lightweight materials that are easily formed and machined, and that may be readily sterilized. Such materials may include titanium or a titanium-based alloy, surgical stainless steel and high strength plastic, although one skilled in the art will recognize that other materials may be employed with similar effect.

In the foregoing description, it can be seen that the present invention comprises a new and useful eye proptosing speculum. It will be appreciated by those skilled in the art that changes could be made to the embodiment described above without departing from the broad inventive concepts thereof. It is understood, therefore, that this invention is not limited to the particular embodiment disclosed, but it is intended to cover modifications within the spirit and scope of the present invention as defined by the impending claims.

I claim:

1. An eye speculum for proptosing an eyeball of a patient, the eyeball having a pair of eyelids associated therewith, the eyeball being positioned in an eye orbit and substantially surrounded by retrobulbar orbital contents within the eye orbit and posterior to the eyelids, the speculum comprising:

an adjustable mechanism having a pair of arms, each arm including a free end spaced an adjustable distance from the free end of the other arm; and a pair of generally posteriorly extending pressors, each pressor being attached to a respective free end of the adjustable mechanism, the pressors being opposingly situated with respect to each other, each pressor being shaped to be inserted behind a respective eyelid and to exert pressure on a peripheral portion of the orbital contents posterior to the respective eyelid, wherein the pressure is transferred by the peripheral portion to a posterior portion of the orbital contents and then to a posterior region of the eyeball to proptose the eyeball outwardly.

2. The eye speculum of claim 1 further comprising a pair of generally posteriorly extending blades opposingly situated with respect to each other, each blade being attached to a respective free end of the adjustable mechanism, each blade having a posterior area and being shaped to engage the patient between one of the eyelids and the eyeball, one pressor extending from each blade at the posterior area thereof.

3. The eye speculum of claim 2 wherein each blade and each pressor is shaped to minimize extrinsic pressure directly on the eyeball.

4. The eye speculum of claim 3 wherein the eyeball has an exterior surface and wherein a portion of each blade adjacent the exterior surface of the eyeball and each pressor, in combination, generally extend to follow the exterior surface of the eyeball.

5. The eye speculum of claim 2 further comprising adjustment means for adjustably fixing the distance between the free ends of the arms.

6. The eye speculum of claim 5 wherein the adjustment means comprises an adjustable screw mechanism.

7. A method for proptosing an eyeball of a patient with an eye speculum, the eyeball having a pair of eyelids associated therewith, the eyeball being positioned in an eye orbit and substantially surrounded by retrobulbar orbital contents within the eye orbit and posterior to the eyelids, the speculum comprising a pair of generally posteriorly extending pressors opposingly situated with respect to each other, the method comprising the steps of:

contacting each pressor to a peripheral portion of the orbital contents;

exerting pressure on each contacted pressor, the pressure being transferred to the peripheral portion, then to a posterior portion of the orbital contents, and then to a posterior region of the eyeball to proptose the eyeball outwardly.

8. The method of claim 7 wherein the speculum further comprises a pair of generally posteriorly extending blades opposingly situated with respect to each other, each blade having a posterior area, one pressor extending from each blade at the posterior area thereof, one blade extending from each arm proximate the free end thereof, the method further comprising the step of engaging each blade to the patient between one of the eyelids and the eyeball.

9. The method of claim 8 wherein the exerting pressure step further comprises exerting pressure on each blade and each pressor while minimizing extrinsic pressure directly on the eyeball.

10. The method of claim 8 wherein the speculum further comprises a pair of adjustable arms, each arm having a free end, one blade being attached to each of the arms proximate the free end thereof, the method further comprising the step of adjusting the distance between the free ends.

\* \* \* \* \*